(12) United States Patent
Adedoyin et al.

US008883410B2

(10) Patent No.: US 8,883,410 B2
(45) Date of Patent: Nov. 11, 2014

(54) METHOD FOR DETERMINING THE STABILITY OF ORGANIC METHYLENEAMINES IN THE PRESENCE OF SEMICARBAZIDE-SENSITIVE AMINE OXIDASE

(71) Applicant: Sanofi, Paris (FR)

(72) Inventors: Adedayo Adedoyin, Stewartsville, NJ (US); Michael R. Angelastro, Bridgewater, NJ (US); Julie Bick, Easton, PA (US); Jennifer Caims, Bridgewater, NJ (US); Yongqing Huang, Flemington, NJ (US); Guyan Liang, Warren, NJ (US); Heng-Keang Lim, Lawrenceville, NJ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/680,068

(22) Filed: Nov. 18, 2012

(65) Prior Publication Data
US 2013/0071870 A1 Mar. 21, 2013

Related U.S. Application Data

(62) Division of application No. 12/518,318, filed as application No. PCT/US2008/050456 on Jan. 8, 2008.

(60) Provisional application No. 60/884,263, filed on Jan. 10, 2007.

(51) Int. Cl.
*C12Q 1/00* (2006.01)
*C12Q 1/26* (2006.01)

(52) U.S. Cl.
CPC ........................................ *C12Q 1/26* (2013.01)
USPC .................................................. 435/4; 435/25

(58) Field of Classification Search
CPC ........................................................ C12Q 1/26
USPC ....................................................... 435/4, 25
See application file for complete search history.

(56) References Cited

U.S. PATENT DOCUMENTS

| 6,977,263 B2 | 12/2005 | Astles et al. |
| 2004/0064842 A1 | 4/2004 | Graham et al. |
| 2005/0255580 A1 | 11/2005 | Vollert |

FOREIGN PATENT DOCUMENTS

| WO | 98/53049 | 11/1998 |
| WO | 02/066669 | 8/2002 |

OTHER PUBLICATIONS

Blicharski et al. "Semicarbazide-sensitive amine oxidase activity in rat aortic cultured smooth muscle cells", J Neural Transm, 1990,[Suppl]32:337-339.*

Precious et al. "Deamination of methylamine by semicarbazide-sensitive amine oxidase in human umbilical artery and rat aorta", Biochemical Pharmacology, 1988, 37(4):707-713.*
Koskinen et al. Granulocyte transmigration through the endothelium is regulated by the oxidase activity of vascular adhesion protein-1 (VAP-1), Boold, 2004, 103(9):338-3395.*
Claud et al. Metabolism of transpermus of rat aorta semicarbazide-sensitive amine oxidase (SSAO), Fundamental & Clinical Pharmacology, 2002, 16:461-470.*
International Search Report in International Application No. PCT/US2008/050456, mailed on Jun. 12, 2008.
International Preliminary Report on Patentability in International Application No. PCT/US2008/05045 report issued Jul. 14, 2009.
Boomsma et al., "Variation in semicarbazide-sensitive amine oxidase activity in plasma and tissues of mammals." Comp. Biochem. Physiol. C Toxicol. Pharmacol. 126(1):69-78 (2000).
Carpene et al., "Short- and long-term insulin-like effects of monoamine oxidases and semicarbazide-sensitive amine oxidase substrates in cultured adipocytes," Metabolism, 55(10):1397-1405 (2006).
Claud et al., "In vitro metabolism of tresperimus by human vascular semicarbazide-sensitive amine oxidase," Drug Metabolism and Disposition, 30(6) 747-55 (2002).
Claud et al., "Metabolism of tresperimus by rat aorta semicarbazide-sensitive amine oxidase (SSAO)" Fundamental and Clinical Pharmacology GB, 16(6):461-70 (2002).
Crosbie & Callingham, "Semicarbazide-sensitive amine oxidases in sheep plasma: interactions with some substrates and inhibitors." J. Neural Transm. Suppl. 41:427-32 (1994).
Elliot et al., "Semicarbazide-sensitive amine oxidase (SSAO) of the rat aorta. Interactions with some naturally occurring amines and their structural analogues," Biochem. Pharmacol. 38(9):1507-15 (1989).
Gong et al., "The role of amine oxidases in xenobiotic metabolism." Expert Opinion on Drug Metabolism & Toxicology 2(4):559-71 (2006).
Koskinen et al. "Granulocyte transmigration through the endothelium is regulated by the oxidase activity vascular adhesion protein-1 (VAP-1)" Blood 103(9):3388-95 (2004).
Kostiainen et al., "Liquid chromatography/atmospheric pressure ionization-mass spectrometry in drug metabolism studies," J. Mass Spectrom. 38:357-72 (2003).
Lyles, "Substrate-specificity of mammalian tissue-bound semicarbazide-sensitive amine oxidase." Prog. Brain Res. 106:293-303 (1995).

(Continued)

*Primary Examiner* — Bin Shen
(74) *Attorney, Agent, or Firm* — McDonnell Boehnen Hulbert & Berghoff LLP

(57) ABSTRACT

The present invention provides methods for determining the stability of methyleneamine, methyleneamine-like compounds or compounds containing a methyleneamine moiety in the presence of semicarbazide-sensitive amine oxidase (SSAO) or a biological sample containing SSAO activity. The disclosed methods may be configured in an assay format for high throughput screening applications.

21 Claims, 4 Drawing Sheets

(56) References Cited

OTHER PUBLICATIONS

Lyles et al., "Further studies on the metabolism of methylamine by semicarbazide-sensitive amine oxidase activities in human plasma, umbilical artery and rat aorta." Journal of Pharmacy and Pharmacology, London 42(5):332-38 (1990).
Precious et al., "Deamination of methylamine by semicarbazide-sensitive amine oxidase in human umbilical artery and rat aorta." Biochem. Pharmacol. 37(4):707-13 (1988).
Sakata et al., "Increase in putrescine, amine oxidase, and acrolein in plasma of renal failure patients," Biochemical and Biophysical Research Communication 305:143-49 (2003).
Smith et al., "Cloning of Vascular Adhesion Protein 1 Reveals a Novel Multifunctional Adhesion Molecule" J Exp. Med. 188(1): 17-27 (1998).
Strolin-Benedetti et al., "Involvement of enzymes other than CYPs in the oxidative metabolism of xenobiotics," Expert Opin. Drug Metab. Toxicol. 2(6):895-921 (2006).
Yegutkin et al., "A peptide inhibitor of vascular adhesion protein-1(VAP-1) blocks leukocyte-endothelium interactions under shear stress," Eur. J. Immunol. 34:2276-85 (2004).
Yraola et al., "New efficient substrates for semicarbazide-sensitive amine oxidase/VAP-1 enzyme: analysis by SARs and computational docking." J. Med. Chem. 49(21):6197-208 (2006).
Gautam et al., "Structural and functional evidence for the role of the TLR2 DD loop in TLR1/TLR2 heterodimerization and signaling." J. Biol. Chem. 281(40):30132-42 (2006).
Paulsen et al., "Epstein-Barr virus-encoded BILF1 is a constitutively active G protein-coupled receptor." J Virol. 79 (1):536-46 (2005).
GenBank AAH33756.1 TLR2 protein of Oct. 7, 2003.
UniProtKB/Swiss-Prot Q16853 (AOC3_HUMAN) of Nov. 1, 1997.
Baranczewski et al., "Introduction to in vitro estimation of metabolic stability and drug interactions of new chemical entities in drug discovery and development," Pharmacol Rep 58(4): 453-72 (2006).
Goturk et al., "Overexpression of semicarbazide-sensitive amine oxidase in smooth muscle cells leads to an abnormal structure of the aortic elastic faminas," Am J Pathol. 163(5): 1921-28 (2003).

* cited by examiner

Amino acid sequence of human SSAO
ACCESSION Q16853

MNQKTILVLL ILAVITIFAL VCVLLVGRGG DGGEPSQLPH CPSVSPSAQP
WTHPGQSQLF    60
ADLSREELTA VMRFLTQRLG PGLVDAAQAR PSDNCVFSVE LQLPPKAAAL
AHLDRGSPPP    120
AREALAIVFF GRQPQPNVSE LVVGPLPHPS YMRDVTVERH GGPLPYHRRP
VLFQEYLDID    180
QMIFNRELPQ ASGLLHHCCF YKHRGRNLVT MTTAPRGLQS GDRATWFGLY
YNISGAGFFL    240
HHVGLELLVN HKALDPARWT IQKVFYQGRY YDSLAQLEAQ FEAGLVNVVL
IPDNGTGGSW    300
SLKSPVPPGP APPLQFYPQG PRFSVQGSRV ASSLWTFSFG LGAFSGPRIF
DVRFQGERLV    360
YEISLQEALA IYGGNSPAAM TTRYVDGGFG MGKYTTPLTR GVDCPYLATY
VDWHFLLESQ    420
APKTIRDAFC VFEQNQGLPL RRHHSDLYSH YFGGLAETVL VVRSMSTLLN
YDYVWDTVFH    480
PSGAIEIRFY ATGYISSAFL FGATGKYGNQ VSEHTLGTVH THSAHFKVDL
DVAGLENWVW    540
AEDMVFVPMA VPWSPEHQLQ RLQVTRKLLE MEEQAAFLVG SATPRYLYLA
SNHSNKWGHP    600
RGYRIQMLSF AGEPLPQNSS MARGFSWERY QLAVTQRKEE EPSSSSVFNQ
NDPWAPTVDF    660
SDFINNETIA GKDLVAWVTA GFLHIPHAED IPNTVTVGNG VGFFLRPYNF
FDEDPSFYSA    720
DSIYFRGDQD AGACEVNPLA CLPQAAACAP DLPAFSHGGF SHN

Figure 1

Nucleotide Sequence of Human SSAO (NM_003734)

```
ATGAACCAGA AGACAATCCT CGTGCTCCTC ATTCTGGCCG TCATCACCAT
CTTTGCCTTG    60
GTTTGTGTCC TGCTGGTGGG CAGGGGTGGA GATGGGGGTG AACCCAGCCA
GCTTCCCCAT   120
TGCCCCTCTG TATCTCCCAG TGCCCAGCCT TGGACACACC CTGGCCAGAG
CCAGCTGTTT   180
GCAGACCTGA GCCGAGAGGA GCTGACGGCT GTGATGCGCT TTCTGACCCA
GCGGCTGGGG   240
CCAGGGCTGG TGGATGCAGC CCAGGCCCGG CCCTCGGACA ACTGTGTCTT
CTCAGTGGAG   300
TTGCAGCTGC CTCCCAAGGC TGCAGCCCTG GCTCACTTGG ACAGGGGGAG
CCCCCCACCT   360
GCCCGGGAGG CACTGGCCAT CGTCTTCTTT GGCAGGCAAC CCCAGCCCAA
CGTGAGTGAG   420
CTGGTGGTGG GGCCACTGCC TCACCCCTCC TACATGCGGG ACGTGACTGT
GGAGCGTCAT   480
GGAGGCCCCC TGCCCTATCA CCGACGCCCC GTGCTGTTCC AAGAGTACCT
GGACATAGAC   540
CAGATGATCT TCAACAGAGA GCTGCCCCAG GCTTCTGGGC TTCTCCACCA
CTGTTGCTTC   600
TACAAGCACC GGGGACGGAA CCTGGTGACA ATGACCACGG CTCCCCGTGG
TCTGCAATCA   660
GGGGACCGGG CCACCTGGTT TGGCCTCTAC TACAACATCT CGGGCGCTGG
GTTCTTCCTG   720
CACCACGTGG GCTTGGAGCT GCTAGTGAAC CACAAGGCCC TTGACCCTGC
CCGCTGGACT   780
ATCCAGAAGG TGTTCTATCA AGGCCGCTAC TACGACAGCC TGGCCCAGCT
GGAGGCCCAG   840
TTTGAGGCCG GCCTGGTGAA TGTGGTGCTG ATCCCAGACA ATGGCACAGG
TGGGTCCTGG   900
TCCCTGAAGT CCCCTGTGCC CCCGGGTCCA GCTCCCCCTC TACAGTTCTA
TCCCCAAGGC   960
CCCCGCTTCA GTGTCCAGGG AAGTCGAGTG GCCTCCTCAC TGTGGACTTT
CTCCTTTGGC  1020
CTCGGAGCAT TCAGTGGCCC AAGGATCTTT GACGTTCGCT TCCAAGGAGA
AAGACTAGTT  1080
TATGAGATAA GCCTCCAAGA GGCCTTGGCC ATCTATGGTG GAAATTCCCC
AGCAGCAATG  1140
ACGACCCGCT ATGTGGATGG AGGCTTTGGC ATGGGCAAGT ACACCACGCC
CCTGACCCGT  1200
GGGGTGGACT GCCCCTACTT GGCCACCTAC GTGGACTGGC ACTTCCTTTT
GGAGTCCCAG  1260
GCCCCCAAGA CAATACGTGA TGCCTTTTGT GTGTTTGAAC AGAACCAGGG
CCTCCCCCTG  1320
CGGCGACACC ACTCAGATCT CTACTCGCAC TACTTTGGGG GTCTTGCGGA
AACGGTGCTG  1380
```

FIG. 2A

GTCGTCAGAT CTATGTCCAC CTTGCTCAAC TATGACTATG TGTGGGATAC
GGTCTTCCAC   1440
CCCAGTGGGG CCATAGAAAT ACGATTCTAT GCCACGGGCT ACATCAGCTC
GGCATTCCTC   1500
TTTGGTGCTA CTGGGAAGTA CGGGAACCAA GTGTCAGAGC ACACCCTGGG
CACGGTCCAC   1560
ACCCACAGCG CCCACTTCAA GGTGGATCTG GATGTAGCAG GACTGGAGAA
CTGGGTCTGG   1620
GCCGAGGATA TGGTCTTTGT CCCCATGGCT GTGCCCTGGA GCCCTGAGCA
CCAGCTGCAG   1680
AGGCTGCAGG TGACCCGGAA GCTGCTGGAG ATGGAGGAGC AGGCCGCCTT
CCTCGTGGGA   1740
AGCGCCACCC CTCGCTACCT GTACCTGGCC AGCAACCACA GCAACAAGTG
GGGTCACCCC   1800
CGGGGCTACC GCATCCAGAT GCTCAGCTTT GCTGGAGAGC CGCTGCCCCA
AAACAGCTCC   1860
ATGGCGAGAG GCTTCAGCTG GAGAGGTAC CAGCTGGCTG TGACCCAGCG
GAAGGAGGAG   1920
GAGCCCAGTA GCAGCAGCGT TTTCAATCAG AATGACCCTT GGGCCCCCAC
TGTGGATTTC   1980
AGTGACTTCA TCAACAATGA GACCATTGCT GGAAAGGATT TGGTGGCCTG
GGTGACAGCT   2040
GGTTTTCTGC ATATCCCACA TGCAGAGGAC ATTCCTAACA CAGTGACTGT
GGGGAACGGC   2100
GTGGGCTTCT TCCTCCGACC CTATAACTTC TTTGACGAAG ACCCCTCCTT
CTACTCTGCC   2160
GACTCCATCT ACTTCCGAGG GACCAGGAT GCTGGGGCCT GCGAGGTCAA
CCCCCTAGCT   2220
TGCCTGCCCC AGGCTGCTGC CTGTGCCCCC GACCTCCCTG CCTTCTCCCA
CGGGGGCTTC   2280
TCTCACAACT AG                              2292

FIG. 2B

SEQUENCE LISTING

<160> NUMBER OF SEQ ID NOS: 18

<210> SEQ ID NO 1
<211> LENGTH: 763
<212> TYPE: PRT
<213> ORGANISM: Homo sapiens

<400> SEQUENCE: 1

```
Met Asn Gln Lys Thr Ile Leu Val Leu Leu Ile Leu Ala Val Ile Thr
1               5                   10                  15

Ile Phe Ala Leu Val Cys Val Leu Leu Val Gly Arg Gly Gly Asp Gly
            20                  25                  30

Gly Glu Pro Ser Gln Leu Pro His Cys Pro Ser Val Ser Pro Ser Ala
        35                  40                  45

Gln Pro Trp Thr His Pro Gly Gln Ser Gln Leu Phe Ala Asp Leu Ser
    50                  55                  60

Arg Glu Glu Leu Thr Ala Val Met Arg Phe Leu Thr Gln Arg Leu Gly
65                  70                  75                  80

Pro Gly Leu Val Asp Ala Ala Gln Ala Arg Pro Ser Asp Asn Cys Val
                85                  90                  95

Phe Ser Val Glu Leu Gln Leu Pro Pro Lys Ala Ala Ala Leu Ala His
            100                 105                 110

Leu Asp Arg Gly Ser Pro Pro Pro Ala Arg Glu Ala Leu Ala Ile Val
        115                 120                 125

Phe Phe Gly Arg Gln Pro Gln Pro Asn Val Ser Glu Leu Val Val Gly
    130                 135                 140

Pro Leu Pro His Pro Ser Tyr Met Arg Asp Val Thr Val Glu Arg His
145                 150                 155                 160

Gly Gly Pro Leu Pro Tyr His Arg Arg Pro Val Leu Phe Gln Glu Tyr
                165                 170                 175

Leu Asp Ile Asp Gln Met Ile Phe Asn Arg Glu Leu Pro Gln Ala Ser
            180                 185                 190

Gly Leu Leu His His Cys Cys Phe Tyr Lys His Arg Gly Arg Asn Leu
        195                 200                 205

Val Thr Met Thr Thr Ala Pro Arg Gly Leu Gln Ser Gly Asp Arg Ala
    210                 215                 220

Thr Trp Phe Gly Leu Tyr Tyr Asn Ile Ser Gly Ala Gly Phe Phe Leu
225                 230                 235                 240

His His Val Gly Leu Glu Leu Leu Val Asn His Lys Ala Leu Asp Pro
                245                 250                 255

Ala Arg Trp Thr Ile Gln Lys Val Phe Tyr Gln Gly Arg Tyr Tyr Asp
            260                 265                 270

Ser Leu Ala Gln Leu Glu Ala Gln Phe Glu Ala Gly Leu Val Asn Val
        275                 280                 285

Val Leu Ile Pro Asp Asn Gly Thr Gly Gly Ser Trp Ser Leu Lys Ser
    290                 295                 300

Pro Val Pro Pro Gly Pro Ala Pro Pro Leu Gln Phe Tyr Pro Gln Gly
305                 310                 315                 320

Pro Arg Phe Ser Val Gln Gly Ser Arg Val Ala Ser Ser Leu Trp Thr
                325                 330                 335

Phe Ser Phe Gly Leu Gly Ala Phe Ser Gly Pro Arg Ile Phe Asp Val
            340                 345                 350

Arg Phe Gln Gly Glu Arg Leu Val Tyr Glu Ile Ser Leu Gln Glu Ala
        355                 360                 365
```

```
Leu Ala Ile Tyr Gly Gly Asn Ser Pro Ala Ala Met Thr Thr Arg Tyr
            370                 375                 380

Val Asp Gly Gly Phe Gly Met Gly Lys Tyr Thr Thr Pro Leu Thr Arg
385                 390                 395                 400

Gly Val Asp Cys Pro Tyr Leu Ala Thr Tyr Val Asp Trp His Phe Leu
                405                 410                 415

Leu Glu Ser Gln Ala Pro Lys Thr Ile Arg Asp Ala Phe Cys Val Phe
            420                 425                 430

Glu Gln Asn Gln Gly Leu Pro Leu Arg Arg His His Ser Asp Leu Tyr
            435                 440                 445

Ser His Tyr Phe Gly Gly Leu Ala Glu Thr Val Leu Val Val Arg Ser
450                 455                 460

Met Ser Thr Leu Leu Asn Tyr Asp Tyr Val Trp Asp Thr Val Phe His
465                 470                 475                 480

Pro Ser Gly Ala Ile Glu Ile Arg Phe Tyr Ala Thr Gly Tyr Ile Ser
                485                 490                 495

Ser Ala Phe Leu Phe Gly Ala Thr Gly Lys Tyr Gly Asn Gln Val Ser
            500                 505                 510

Glu His Thr Leu Gly Thr Val His Thr His Ser Ala His Phe Lys Val
            515                 520                 525

Asp Leu Asp Val Ala Gly Leu Glu Asn Trp Val Trp Ala Glu Asp Met
530                 535                 540

Val Phe Val Pro Met Ala Val Pro Trp Ser Pro Glu His Gln Leu Gln
545                 550                 555                 560

Arg Leu Gln Val Thr Arg Lys Leu Leu Glu Met Glu Glu Gln Ala Ala
                565                 570                 575

Phe Leu Val Gly Ser Ala Thr Pro Arg Tyr Leu Tyr Leu Ala Ser Asn
            580                 585                 590

His Ser Asn Lys Trp Gly His Pro Arg Gly Tyr Arg Ile Gln Met Leu
            595                 600                 605

Ser Phe Ala Gly Glu Pro Leu Pro Gln Asn Ser Ser Met Ala Arg Gly
610                 615                 620

Phe Ser Trp Glu Arg Tyr Gln Leu Ala Val Thr Gln Arg Lys Glu Glu
625                 630                 635                 640

Glu Pro Ser Ser Ser Ser Val Phe Asn Gln Asn Asp Pro Trp Ala Pro
                645                 650                 655

Thr Val Asp Phe Ser Asp Phe Ile Asn Asn Glu Thr Ile Ala Gly Lys
            660                 665                 670

Asp Leu Val Ala Trp Val Thr Ala Gly Phe Leu His Ile Pro His Ala
            675                 680                 685

Glu Asp Ile Pro Asn Thr Val Thr Val Gly Asn Gly Val Gly Phe Phe
690                 695                 700

Leu Arg Pro Tyr Asn Phe Phe Asp Glu Asp Pro Ser Phe Tyr Ser Ala
705                 710                 715                 720

Asp Ser Ile Tyr Phe Arg Gly Asp Gln Asp Ala Gly Ala Cys Glu Val
                725                 730                 735

Asn Pro Leu Ala Cys Leu Pro Gln Ala Ala Cys Ala Pro Asp Leu
            740                 745                 750

Pro Ala Phe Ser His Gly Gly Phe Ser His Asn
            755                 760

<210> SEQ ID NO 2
<211> LENGTH: 2292
<212> TYPE: DNA
```

<213> ORGANISM: Homo sapiens

<400> SEQUENCE: 2

| | | | | | |
|---|---|---|---|---|---|
| atgaaccaga | agacaatcct | cgtgctcctc | attctggccg | tcatcaccat | ctttgccttg | 60 |
| gtttgtgtcc | tgctggtggg | caggggtgga | gatggggtg | aacccagcca | gcttccccat | 120 |
| tgcccctctg | tatctcccag | tgcccagcct | tggacacacc | ctggccagag | ccagctgttt | 180 |
| gcagacctga | gccgagagga | gctgacggct | gtgatgcgct | ttctgaccca | gcggctgggg | 240 |
| ccagggctgg | tggatgcagc | ccaggcccgg | ccctcggaca | actgtgtctt | ctcagtggag | 300 |
| ttgcagctgc | ctcccaaggc | tgcagccctg | gctcacttgg | acaggggag | ccccccacct | 360 |
| gcccgggagg | cactggccat | cgtcttcttt | ggcaggcaac | cccagcccaa | cgtgagtgag | 420 |
| ctggtggtgg | ggccactgcc | tcacccctcc | tacatgcggg | acgtgactgt | ggagcgtcat | 480 |
| ggaggccccc | tgccctatca | ccgacgcccc | gtgctgttcc | aagagtacct | ggacatagac | 540 |
| cagatgatct | tcaacagaga | gctgccccag | gcttctgggc | ttctccacca | ctgttgcttc | 600 |
| tacaagcacc | ggggacggaa | cctggtgaca | atgaccacgg | ctccccgtgg | tctgcaatca | 660 |
| ggggaccggg | ccacctggtt | tggcctctac | tacaacatct | cgggcgctgg | gttcttcctg | 720 |
| caccacgtgg | gcttggagct | gctagtgaac | cacaaggccc | ttgaccctgc | ccgctggact | 780 |
| atccagaagg | tgttctatca | aggccgctac | tacgacagcc | tggcccagct | ggaggcccag | 840 |
| tttgaggccg | gctggtgaa | tgtggtgctg | atcccagaca | atggcacagg | tgggtcctgg | 900 |
| tccctgaagt | cccctgtgcc | ccgggtccca | gctccccctc | tacagttcta | tccccaaggc | 960 |
| ccccgcttca | gtgtccaggg | aagtcgagtg | gcctcctcac | tgtggacttt | ctcctttggc | 1020 |
| ctcggagcat | tcagtggccc | aaggatcttt | gacgttcgct | tccaaggaga | aagactagtt | 1080 |
| tatgagataa | gcctccaaga | ggccttggcc | atctatggtg | gaaattcccc | agcagcaatg | 1140 |
| acgacccgct | atgtggatgg | aggctttggc | atgggcaagt | acaccacgcc | cctgacccgt | 1200 |
| gggtggact | gcccctactt | ggccacctac | gtggactggc | acttccttttt | ggagtcccag | 1260 |
| gcccccaaga | caatacgtga | tgccttttgt | gtgtttgaac | agaaccaggg | cctccccctg | 1320 |
| cggcgacacc | actcagatct | ctactcgcac | tactttgggg | gtcttgcgga | aacggtgctg | 1380 |
| gtcgtcagat | ctatgtccac | cttgctcaac | tatgactatg | tgtgggatac | ggtcttccac | 1440 |
| cccagtgggg | ccatagaaat | acgattctat | gccacgggct | acatcagctc | ggcattcctc | 1500 |
| tttggtgcta | ctgggaagta | cgggaaccaa | gtgtcagagc | acaccctggg | cacggtccac | 1560 |
| acccacagcg | cccacttcaa | ggtggatctg | gatgtagcag | gactggagaa | ctgggtctgg | 1620 |
| gccgaggata | tggtctttgt | ccccatggct | gtgccctgga | gccctgagca | ccagctgcag | 1680 |
| aggctgcagg | tgacccggaa | gctgctgag | atggaggagc | aggccgcctt | cctcgtggga | 1740 |
| agcgccaccc | ctcgctacct | gtacctggcc | agcaaccaca | gcaacaagtg | gggtcacccc | 1800 |
| cggggctacc | gcatccagat | gctcagcttt | gctggagagc | cgctgcccca | aaacagctcc | 1860 |
| atggcgagag | gcttcagctg | ggagaggtac | cagctggctg | tgacccagcg | gaaggaggag | 1920 |
| gagcccagta | gcagcagcgt | tttcaatcag | aatgaccctt | gggcccccac | tgtggatttc | 1980 |
| agtgacttca | tcaacaatga | gaccattgct | ggaaaggatt | tggtgccctg | ggtgacagct | 2040 |
| ggttttctgc | atatcccaca | tgcagaggac | attcctaaca | cagtgactgt | ggggaacggc | 2100 |
| gtgggcttct | cctccgacc | ctataacttc | tttgacgaag | acccctcctt | ctactctgcc | 2160 |
| gactccatct | acttccagagg | ggaccaggat | gctgggcct | gcgaggtcaa | ccccctagct | 2220 |
| tgcctgcccc | aggctgctgc | ctgtgccccc | gacctccctg | ccttctccca | cggggcttc | 2280 |

-continued tctcacaact ag                                                    2292

<210> SEQ ID NO 3
<211> LENGTH: 37
<212> TYPE: DNA
<213> ORGANISM: Artificial
<220> FEATURE:
<223> OTHER INFORMATION: initial cloning primer - forward

<400> SEQUENCE: 3
aaaagcaggc ttaggaatga accagaagac aatcctc                         37

<210> SEQ ID NO 4
<211> LENGTH: 35
<212> TYPE: DNA
<213> ORGANISM: Artificial
<220> FEATURE:
<223> OTHER INFORMATION: initial cloning primer - reverse

<400> SEQUENCE: 4
caagaaagct gggtcctagt tgtgagagaa gcccc                           35

<210> SEQ ID NO 5
<211> LENGTH: 34
<212> TYPE: DNA
<213> ORGANISM: Artificial
<220> FEATURE:
<223> OTHER INFORMATION: universal primer - forward

<400> SEQUENCE: 5
ggggacaagt ttgtacaaaa aagcaggctt agga                            34

<210> SEQ ID NO 6
<211> LENGTH: 30
<212> TYPE: DNA
<213> ORGANISM: Artificial
<220> FEATURE:
<223> OTHER INFORMATION: universal primer - reverse

<400> SEQUENCE: 6
ggggaccact ttgtacaaga aagctgggtc                                 30

<210> SEQ ID NO 7
<211> LENGTH: 37
<212> TYPE: DNA
<213> ORGANISM: Artificial
<220> FEATURE:
<223> OTHER INFORMATION: forward primer sequence for cloning untagged
      full-length SSAO

<400> SEQUENCE: 7
aaaagcaggc ttaggaatga accagaagac aatcctc                         37

<210> SEQ ID NO 8
<211> LENGTH: 40
<212> TYPE: DNA
<213> ORGANISM: Artificial
<220> FEATURE:
<223> OTHER INFORMATION: reverse primer sequence for cloning untagged
      full-length SSAO

<400> SEQUENCE: 8
caagaaagct gggtcctagt tgtgagagaa gcccccgtgg                      40

<210> SEQ ID NO 9

-continued

```
<211> LENGTH: 37
<212> TYPE: DNA
<213> ORGANISM: Artificial
<220> FEATURE:
<223> OTHER INFORMATION: forward primer sequence for cloning full-length
      SSAO with C-terminal 6xHIS tag

<400> SEQUENCE: 9
aaaagcaggc ttaggaatga accagaagac aatcctc                                37

<210> SEQ ID NO 10
<211> LENGTH: 58
<212> TYPE: DNA
<213> ORGANISM: Artificial
<220> FEATURE:
<223> OTHER INFORMATION: reverse primer sequences for cloning
      full-length SSAO with C-terminal 6xHIS tag

<400> SEQUENCE: 10
caagaaagct gggtcctaat ggtgatggtg atggtggttg tgagagaagc ccccgtgg        58

<210> SEQ ID NO 11
<211> LENGTH: 41
<212> TYPE: DNA
<213> ORGANISM: Artificial
<220> FEATURE:
<223> OTHER INFORMATION: forward primer sequences for cloning N-terminal
      truncated untagged SSAO

<400> SEQUENCE: 11
aaaagcaggc ttaggaatgg gcaggggtgg agatgggggt g                          41

<210> SEQ ID NO 12
<211> LENGTH: 35
<212> TYPE: DNA
<213> ORGANISM: Artificial
<220> FEATURE:
<223> OTHER INFORMATION: reverse primer sequences for cloning N-terminal
      truncated untagged SSAO

<400> SEQUENCE: 12
caagaaagct gggtcctagt tgtgagagaa gcccc                                 35

<210> SEQ ID NO 13
<211> LENGTH: 41
<212> TYPE: DNA
<213> ORGANISM: Artificial
<220> FEATURE:
<223> OTHER INFORMATION: forward primer sequences for cloning N-terminal
      truncated C-terminal 6xHIS tag SSAO

<400> SEQUENCE: 13
aaaagcaggc ttaggaatgg gcaggggtgg agatgggggt g                          41

<210> SEQ ID NO 14
<211> LENGTH: 58
<212> TYPE: DNA
<213> ORGANISM: Artificial
<220> FEATURE:
<223> OTHER INFORMATION: reverse primer sequences for cloning N-terminal
      truncated C-terminal 6xHIS tag SSAO

<400> SEQUENCE: 14
caagaaagct gggtcctaat ggtgatggtg atggtggttg tgagagaagc ccccgtgg        58

<210> SEQ ID NO 15
<211> LENGTH: 38
```

```
<212> TYPE: DNA
<213> ORGANISM: Artificial
<220> FEATURE:
<223> OTHER INFORMATION: forward primer sequences for cloning catalytic
      domain of untagged SSAO

<400> SEQUENCE: 15
aaaagcaggc ttaggaatga ccacggctcc ccgtggtc                              38

<210> SEQ ID NO 16
<211> LENGTH: 35
<212> TYPE: DNA
<213> ORGANISM: Artificial
<220> FEATURE:
<223> OTHER INFORMATION: reverse primer sequences for cloning catalytic
      domain of untagged SSAO

<400> SEQUENCE: 16
caagaaagct gggtcctagt tgtgagagaa gcccc                                 35

<210> SEQ ID NO 17
<211> LENGTH: 38
<212> TYPE: DNA
<213> ORGANISM: Artificial
<220> FEATURE:
<223> OTHER INFORMATION: forward primer sequences for cloning catalytic
      domain of SSAO with C-terminal 6xHIS tag

<400> SEQUENCE: 17
aaaagcaggc ttaggaatga ccacggctcc ccgtggtc                              38

<210> SEQ ID NO 18
<211> LENGTH: 58
<212> TYPE: DNA
<213> ORGANISM: Artificial
<220> FEATURE:
<223> OTHER INFORMATION: reverse primer sequences for cloning catalytic
      domain of SSAO with C-terminal 6xHIS tag

<400> SEQUENCE: 18
caagaaagct gggtcctaat ggtgatggtg atggtggttg tgagagaagc ccccgtgg        58
```

METHOD FOR DETERMINING THE STABILITY OF ORGANIC METHYLENEAMINES IN THE PRESENCE OF SEMICARBAZIDE-SENSITIVE AMINE OXIDASE

This application is a division of U.S. application Ser. No. 12/518,318, filed Jun. 9, 2009, which was a national stage application under 35 U.S.C. §371 of International Application No. PCT/US2008/050456, filed Jan. 8, 2008, which claims the benefit of U.S. Provisional Application No. 60/884,263, filed Jan. 10, 2007, the disclosures of each of which are explicitly incorporated by reference herein.

The present invention provides methods for determining the stability of methyleneamine, methyleneamine-like compounds or compounds containing an methyleneamine moiety in the presence of semicarbazide-sensitive amine oxidase (SSAO) or a biological sample containing SSAO activity. The disclosed methods may be configured in an assay format for high throughput screening applications.

BACKGROUND OF THE INVENTION

Semicarbazide-sensitive amine oxidases (SSAO) are widely distributed in tissues, particularly in blood vessels, suggesting a role for this enzyme for inactivating circulating methyleneamines (Lyles, Prog. Brain Res., 106:293-303, 1995). Many investigators have focused their efforts on finding an endogenous ligand for SSAO and on looking for inhibitors of this enzyme (Precious et al., Biochem. Pharmacol., 37:707-713, 1988; Crosbie and Callingham, J. Neural Transm. Suppl., 41:427-432, 1994; Elliot et al., Biochem. Pharmacol. 38:1507-1515, 1989; Boomsma et al., Comp. Biochem. Physiol. C Toxicol. Pharmacol., 126:69-78, 2000; Yraola et al., J. Med. Chem. 49:6197-6208; WO 02/066669). Others have searched for alternative physiological roles of SSAO. For example, SSAO, also called vascular adhesion protein-1 (VAP-1), has been shown to be up-regulated under inflammatory conditions and to mediate the binding of lymphocytes (WO 98/53049). The instant invention utilizes the enzyme activity of SSAO to measure the metabolic stability of test agents in cells and biological samples.

Metabolic stability of test agents has become a critical factor in drug development, thus, the instant invention solves the problem of identifying potential test agents that are subject to metabolism by SSAO. Advances in chemistry, molecular biology and high-throughput technology have provided drug discovery programs with the ability to screen an enormous number of compounds against a large number of targets to identify lead compounds. These leads then undergo more selection criteria to identify those compounds with optimal "drug-like" properties (i.e., adequate physico-chemical stability, solubility, safety, efficacy, in vivo disposition). Significant efforts are directed toward identifying and eliminating compounds (or compound classes) that are not likely to have "drug-like" properties at earlier stages of discovery. The three main reasons a drug fails during clinical trials are lack of efficacy, unacceptable adverse effects, and unfavorable ADME (absorption, distribution, metabolism, excretion) properties. Therefore the ultimate success of a compound is not only defined by its biological activity and potency, but also by its ADME/toxicity properties. As a result, lead optimization programs have incorporated screens to select drugs with desirable ADME/toxicity properties to enhance the likelihood that new lead compounds will have success in the clinic. Metabolic transformation of drug molecules represents a key process by which drugs are cleared from the body.

Given the wide distribution of SSAO in many bodily compartments, we believe SSAO may be an important enzyme that contributes to a drug's potential metabolic liability. Thus, the instant invention uses methods of determining the metabolic stability of test agents exposed to SSAO. Methods directed to determining the metabolism of a drug or other test agent by enzymes involved in biotransformation, in particular SSAO, have important implications for drug development.

In in vitro studies, compound A (U.S. Pat. No. 6,977,263 B) was incubated with plasma of various species including human. Compound A was observed to be more stable in human plasma in comparison to sheep, guinea pig, rat, and mouse up to one hour. Additionally, no significant metabolism or degradation was observed for the compound in human plasma up to 4 hours with or without semicarbazide. However, pharmacokinetic data from the "first in man" study showed that the same compound was rapidly metabolized and to a far greater extent than that demonstrated in vitro using plasma from human and from other species. Subsequent studies confirmed that membrane-bound SSAO was primarily responsible for the metabolism of the compound in man. These data indicate that soluble SSAO found in human plasma does not possess the same level of enzyme activity and/or substrate specificity as the membrane bound SSAO under physiological conditions. Therefore, as illustrated by compound A, measuring human plasma stability is not predictive of SSAO stability in man and thus is of limited utility in selecting pharmaceutical agents as clinical candidates.

BRIEF DESCRIPTION OF THE DRAWINGS

FIG. 1 shows the amino acid sequence of human SSAO (Genbank Accession No. Q16853; SEQ ID NO: 1).

FIG. 2 shows the nucleotide sequence of human SSAO (Genbank Accession No. NM_00374; SEQ ID NO: 2).

DETAILED DESCRIPTION OF THE INVENTION

Figure 3:
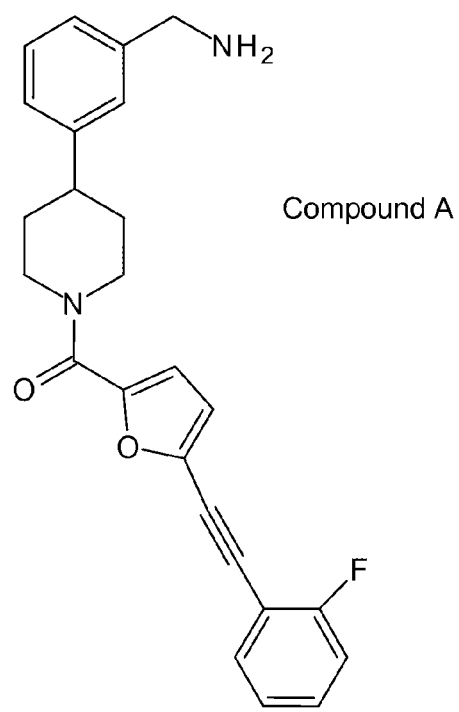
FIG. 3 shows the chemical structure of compound A.

All publications cited herein are hereby incorporated by reference. Unless defined otherwise, all technical and scientific terms used herein have the same meaning as commonly understood to one of ordinary skill in the art to which this invention pertains.

The terminology used in this specification and the appended claims is for the purpose of describing particular embodiments only and the use in the specification is not intended to be limiting of the invention. The singular forms of a word are intended to include the plural forms unless the context clearly indicates otherwise. For example, the singular forms of "a", "an" and "the" are intended to include the plural forms as well. Further, reference to an agent may include a mixture of two or more agents. Thus, the term "an agent" includes a plurality of agents, including mixtures and/or enantiomers thereof. It should also be noted that the term "or" is generally employed in its sense including "and/or" unless the content clearly dictates otherwise. It will be further understood that the terms "comprises" and/or "comprising," when used in this specification, specify the presence of stated features, steps, elements, and/or components, but do not preclude the presence or addition of one or more other features, steps, elements, components, and/or groups thereof.

Furthermore, in accordance with the present invention there may be employed conventional molecular biology, microbiology, recombinant DNA and analytical techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription and Translation [B. D. Hames & S. J. Higgins, eds. (1984)]; Animal Cell Culture [R. I. Freshney, ed. (1986)]; Immobilized Cells and Enzymes [IRL Press, (1986)]; B. Perbal, A Practical Guide to Molecular Cloning (1984); F. M. Ausubel et al. (eds.), Current Protocols in Molecular Biology, John Wiley & Sons, Inc. (1994); A Handbook of Bioanalysis and Drug Metabolism, G. Evans (2004).

An embodiment of the present invention is a method of identifying metabolic stability of a test agent due to semicarbazide-sensitive amine oxidase (SSAO) catalyzed metabolism, the method comprising: (a) culturing cells expressing SSAO; (b) adding a test agent to the cells; (c) incubating the test agent with the cells for a predetermined period of time; (d) measuring the amount of the test agent remaining in the presence of the cells comprising expressed SSAO at the predetermined period of time; and (e) comparing the amount of the test agent at the predetermined period of time to the amount of test agent in a control to determine a value wherein the value identifies the metabolic stability of the test agent in the presence of cells comprising expressed SSAO.

One skilled in the art will recognize that the method may be carried out using the cell lysate instead of the cells. Thus, an embodiment of the present invention is a method of identifying the metabolic stability of a test agent due to semicarbazide-sensitive amine oxidase (SSAO) catalyzed metabolism, the method comprising: (a) culturing cells expressing SSAO; (b) lysing the cells to form a cell lysate; (c) adding a test agent to the cell lysate; (d) incubating the test agent with the cell lysate for a predetermined period of time; (e) measuring the amount of the test agent remaining in the presence of the cell lysate comprising expressed SSAO at the predetermined period of time; and (f) comparing the amount of the test agent at the predetermined period of time to the amount of test agent in a control to determine a value wherein the value identifies the metabolic stability of the test agent in the presence of cell lysate comprising expressed SSAO. Another embodiment combines steps (b) and (c) into a single step.

A further embodiment of the present invention is a method of identifying the metabolic stability of a test agent due to SSAO catalyzed metabolism in a biological sample, the method comprising: (a) obtaining a biological sample comprising SSAO; (b) adding a test agent to the biological sample; (c) incubating the test agent with the biological sample for a predetermined period of time; (d) measuring the amount of the test agent at the predetermined period of time; and (e) comparing the amount of the test agent at the predetermined period of time to the amount of test agent in a control to determine a value wherein the value identifies the metabolic stability of the test agent in the presence of a biological sample comprising SSAO.

An embodiment of the present invention uses primary cell culture or cell lines that are commercially available. As a non-limiting example, cells that can be used are available from the American Tissue Culture Company. In one embodiment, CHO cells are used. Cells may be prokaryotic or eukaryotic. The scope of the invention is not limited by the type of cells used.

A biological sample may include, but is not limited to, tissue or fluids, sections of tissues such as biopsy and autopsy samples, and frozen sections taken for histologic purposes. Such samples include blood, sputum, tissue, cultured cells, (e.g., primary cultures, explants, and transformed cells), parts of or whole organs (e.g., liver, lung, ileum, artery, umbilical cord), stool, urine, etc. A biological sample can be obtained from an eukaryotic organism, including from mammals such as a primate, e.g., chimpanzee, macaque or human, cow, dog, cat, a rodent, e.g., guinea pig, rat, mouse, rabbit, or a bird, reptile, or fish. A non-limiting example of one embodiment of the instant invention is to investigate whether a particular test agent or compound has greater risk for metabolic liability or conversely is metabolically stable in one tissue compartment versus other tissue compartments, e.g., whether a compound has greater metabolic stability in liver compared to lung. Further, a biological sample can be processed to provide a suspension of its cellular components or used for primary culture of the cellular components.

An embodiment of the invention is to use a biological sample from a human or non-human subject to quantitate the metabolic stability of a test agent. A biological sample may be an organ sample derived from one or more organs of non-human animals or humans, a tissue sample derived from one or more tissues of non-human animals or humans, as well as cell samples, derived from one or more cells of non-human animals or humans or from cell cultures. For animal experimentation, biological samples may comprise target organ tissues obtained, for example, after necropsy or biopsy or may be body fluids, such as blood. For clinical use, samples may comprise body fluids, like blood, sera, plasma, urine, synovial fluid, spinal fluid, cerebrospinal fluid, semen or lymph, as well as body tissues obtained by biopsy. A reference or control is understood by one skilled in the art. A reference or control can include, but is not limited to, a biological sample from a non-diseased subject wherein the subject is a non-human animal or human. Further, a reference or control can be a biological sample from a non-treated subject. Alternatively, a reference or control can be from the same subject before, during and after treatment. A reference or control can be from the same subject but is a different cell, tissue or organ sample than the cell, tissue or organ source used to identify the metabolic stability of the test agent. A reference or control does not have to be a biological sample but can be a sample with a known amount of SSAO activity. A reference or control may be an agent that is not metabolized by SSAO or that is metabolized by SSAO with a known amount of SSAO liability.

The present invention provides methods for identifying the metabolic stability or metabolic liability of test agents. The term "test agent" as used herein describes any molecule, e.g. protein, non-protein organic compound or pharmaceutical, with the capability of being affected by or affecting the enzyme activity of SSAO. There are no particular restrictions as to the test agents that can be assayed. In an embodiment of the invention, a test agent is a compound. Examples of test agents include single agents or libraries of small, medium or high molecular weight chemical molecules. An agent can be in the form of a library of test agents, such as a combinatorial or randomized library that provides a sufficient range of diversity or conversely are limited to similar structures or features. Agents can be optionally linked to a fusion partner, e.g., targeting compounds, rescue compounds, dimerization compounds, stabilizing compounds, addressable compounds, and other functional moieties. Conventionally, new chemical entities with useful properties are generated by identifying a test agent (called a "lead compound" or a "lead") with some desirable property or activity, e.g., inhibiting activity or modulating activity. The lead compound is then used as a scaffold to create variants of the lead compound, and further evaluate the property and activity of those variant compounds. One skilled in the art will appreciate the utility of using the instant invention to optimize compound selection by identifying metabolic stability and thus the metabolic liability of potential lead compounds and identifying or selecting those compounds with minimal liability to SSAO metabolism.

SSAO of the present invention is full-length SSAO or a fragment thereof that retains total or partial enzyme activity. Partial enzyme activity may be 30% of the total enzyme activity or greater, for example, 40% or 50%. A non-limiting example is an SSAO isolated from a species other than human. Non-limiting examples of other species include rodents such as rats, mice and guinea pigs or non-human primates such as monkeys or chimpanzees. A further non-limiting example is full-length human SSAO as disclosed in SEQ ID NO: 1 or fragments thereof having methyleneamine oxidase activity.

Metabolic stability or metabolic liability are terms of art understood by the skilled artisan. Metabolic stability refers to the susceptibility or extent to which a test agent or a drug molecule undergoes metabolism under a given condition. Thus, the higher the extent of metabolism, the lower the metabolic stability. Metabolic stability is one of several major determinants in defining the oral bioavailability and systemic clearance of a drug, compound or test agent. As a non-limiting illustration, after a drug is administered orally, it first encounters metabolic enzymes in the gastrointestinal lumen as well as in the intestinal epithelium. After it is absorbed into the bloodstream through the intestinal epithelium, it is delivered to the liver via the portal vein. A drug can be effectively cleared by intestinal or hepatic metabolism before it reaches systemic circulation, a process known as first pass metabolism. The stability or liability of a drug to metabolism within the liver as well as extra-hepatic tissues will ultimately determine the concentration of drug found in the systemic circulation and affect its half-life and residence time within the body. The type of biotransformations typically referred to as Phase I metabolism include oxidation, reduction, and hydrolysis which primarily serve to increase the hydrophilicity and enhance the excretion of a drug by unveiling or incorporating a polar functional group into the molecule (OH, SH, $NH_2$, or $CO_2H$). Phase II reactions or conjugation reactions further increase the polarity of a drug by modifying a functional group to form O- or N-glucuronides, sulfate esters, alpha-carboxyamides and glutathionyl adducts. An embodiment of the instant invention is the metabolic stability or metabolic liability of a drug, compound or test agent to metabolism by SSAO.

An embodiment of the invention selects the most relevant biological samples from human and other species to examine metabolic stability due to SSAO metabolism. For instance, liver-based metabolism is responsible for metabolic clearance of most drugs so concern in first pass metabolism may focus on hepatic and sometimes intestinal metabolism. The ubiquitous presence of SSAO in tissues and biological fluids and its particularly high activity in many tissues, such as lung and blood vessels, makes it imperative to use the appropriate biological samples in addition to or in place of liver to examine a test agent's metabolic stability in the presence of SSAO. In addition to intestinal and hepatic first-pass metabolism, the exposure of a test agent subject to SSAO may be limited by first pass metabolism at sites other than intestinal and hepatic tissues, such as portal veins, blood vessels, and lungs. A test agent may demonstrate different metabolic stability against different forms of SSAO. Different biological samples may contain different forms of SSAO. A non-limiting example is that a test agent may show relative metabolic stability against the soluble form of SSAO in human plasma but much higher metabolic instability against membrane-bound SSAO in tissues. Additionally, an animal species may show much higher or lower soluble SSAO activity in plasma than the level of soluble SSAO activity found in human, under comparable assay conditions.

An embodiment of the invention uses various chemical inhibitors to inhibit various forms of amine oxidase activities and attributes the observed metabolic instability as either SSAO catalyzed or monoamine oxidase (MAO)-A or MAO-B catalyzed metabolism. A non-limiting example is the addition of hydralazine as a non-discriminating amine oxidase inhibitor, clorgyline as a specific MAO-A inhibitor, pargyline as a mixed MAO-A and MAO-B inhibitor, semicarbazide and bromoethylamine as specific SSAO inhibitors.

Another non-limiting example of the invention is to determine the metabolic stability of a test agent in individuals treated with a drug or a combination of drugs to determine if there is a change in the metabolic stability of the test agent in such individuals compared to control subjects. One skilled in the art will appreciate the usefulness of obtaining biological samples from human or non-human subjects that suffer from one or more diseases or have been manipulated to induce one or more disease states, surgically or genetically altered or pretreated with a drug, compound or test agent. A non-limiting example includes using the invention to determine the metabolic stability of a test agent in organs that may be compromised by disease compared to non-diseased organs. As an additional non-limiting example, the metabolic stability of a compound can be assessed in lung tissue obtained from a human subject suffering from asthma and compared to the metabolic stability of the compound in healthy lung tissue from an age-matched or control subject. Another non-limiting example would be to study the metabolic stability of a compound in a biological sample such as in "young" liver compared to "old" or "aged" liver where "young", "old" and "aged" are defined by the particular species under investigation.

An embodiment of the invention uses a homogeneous cell population or one biological sample. An alternative embodiment of the invention uses a heterogeneous cell population or a combination of more than one biological sample. The cells or biological sample can be of any type and in any proportion to complete the methods of the invention.

An embodiment of the invention uses a recombinant cell expressing SSAO. A recombinant expression vector of the invention comprises a nucleic acid molecule in a form suitable for expression of the nucleic acid in a host cell. Thus, a recombinant expression vector of the present invention can include one or more regulatory sequences, selected on the basis of the host cells to be used for expression, that is operably linked to the nucleic acid to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology Vol. 185, Academic Press, San Diego, Calif. (1990). Regulatory sequences include those that direct constitutive expression of the nucleotide sequence in many types of host cells (e.g., tissue specific regulatory sequences). It will be appreciated by those skilled in the art that the design of the expression vector can depend on such factors as the choice of host cell to be transformed, the level of expression of protein desired, etc. The expression vectors of the invention can be introduced into host cells to produce proteins or peptides encoded by nucleic acids as described herein.

The term "overexpression" as used herein, refers to the expression of a polypeptide at a level that is greater than the normal level of expression of the polypeptide in a cell that normally expresses the polypeptide or in a cell that does not normally express the polypeptide. For example, expression of the polypeptide may by 10%, 20%, 30%, 40%, 50%, 60%, 70, 80%, 90%, 100%, or more as compared to expression of the polypeptide in a wild-type cell that normally expresses the polypeptide. Mutants, variants, or analogs of the polypeptide of interest may be overexpressed.

As used herein, the term "transient" expression refers to expression of exogenous nucleic acid molecule(s) which are separate from the chromosomes of the cell. Transient expression generally reaches its maximum 2-3 days after introduction of the exogenous nucleic acid and subsequently declines.

As used here, the term "stable" expression refers to expression of exogenous nucleic acid molecule(s) that have become an integrated part of the chromosome(s) of the cell. In general, vectors for stable expression of genes include one or more selection markers.

Cell culturing techniques for transformed, non-transformed, primary culture and biological samples are well known in the art. Biological samples or cultured cells can be stored until required for use. The media used for culturing can be specifically designed or purchased from commercial sources.

An embodiment of the invention involves lysing the cells. Cells can be lysed by the addition of a detergent containing lysis buffer. However, the invention is not limited to the use of detergent in the lysis buffer but may include any method that is appropriate for lysing cells. For example, cells may be lysed by exposure to hypertonic buffer, sonication or freeze/thaw. These and other methods of lysing cells are well known to those skilled in the art.

An embodiment of the invention uses a control. A control is a term of art well understood by skilled artisans. An appropriate control may be dependent on the assay parameters utilized or the experimental question under investigation. A control may be a particular set of assay conditions or the addition or elimination of a particular compound to the assay. Therefore, a non-limiting example of a control is a condition where a test agent is incubated in the absence of cells or cell lysates expressing SSAO. A control may be considered a positive control in that the assay conditions or control compound added brings about the anticipated response. For example, if the agent under investigation is expected to be metabolized, a positive control would be a compound that is metabolized by SSAO. Further, a positive control may be a compound that is metabolized by SSAO into known metabolic by-products. A non-limiting example of a positive control is the addition of benzylamine. A control may also be a negative control. A negative control may be a particular set of assay conditions or the addition or elimination of a particular compound to the assay that would not bring about the anticipated response. For example, if the agent under investigation is expected to be metabolized, then a negative control would be expected not to be metabolized. A non-limiting example of a negative control is the addition of benzyoic acid that does not have a methyleneamine group and is not metabolized by SSAO. A non-limiting example of a particular set of assay conditions as a negative control may be the addition of an inhibitor targeting SSAO enzyme activity, such as hydralazine, wherein the SSAO activity is inhibited. A control may be a "vehicle" control. For example, if the test agent is dissolved in DMSO then the vehicle control would be DMSO without test agent. A control may simply be the use of historical data.

An embodiment of the present invention is measuring the amount of the test agent incubated in the presence of SSAO at the predetermined period of time and comparing the amount of the test agent at the predetermined period of time to the amount of test agent in a control to determine the metabolic stability of the test agent in the presence of SSAO. It is readily apparent to one skilled in the art that metabolic stability of test agent can be measured by the disappearance of the test agent or alternatively by measuring the appearance of one or more metabolites of the test agent. A further embodiment of the present invention is to measure the appearance of one or more metabolites of the test agent in addition to or in place of measuring the amount of test agent.

The amount of test agent or the appearance of one or more metabolites of the test agent can be measured by any number of techniques available to one skilled in the art. Non-limiting examples include mass spectrometry, high-pressure liquid chromatography (HPLC), liquid chromatography/mass spectrometry, liquid chromatography/mass spectrometry/mass spectrometry and liquid chromatography/radiomatic detection. Further, the amount of test agent or the appearance of one or more metabolites of the test agent may be measured by the use of indicator molecules such as radioisotopes, fluorescent dyes or antibodies. The instant invention is not limited by the method of measuring the test agent or any one or more metabolites of the test agent.

The test agent may be labeled with a radioisotope, such as, but not limited to $^3$H or $^{14}$C. Thus, an embodiment of the invention is a method of identifying the metabolic stability of a radiolabeled test agent due to semicarbazide-sensitive amine oxidase (SSAO) catalyzed metabolism, the method comprising: (a) culturing cells expressing SSAO; (b) adding a radiolabeled test agent to the cells; (c) incubating the radiolabeled test agent with the cells for a predetermined period of time; and (d) measuring the amount of the radiolabeled test agent remaining in the presence of the cells comprising expressed SSAO at the predetermined period of time wherein the percentage of radiolabeled test agent that has not been metabolized identifies the metabolic stability of the radiolabeled test agent in the presence of cells comprising expressed SSAO. One skilled in the art will recognize the method may be carried out using cell lysates instead of the cells. Further, the instant invention is not limited by the use of radioisotopes but may use any means available in the art to label the test agent.

A further embodiment of the present invention is a method of identifying metabolic stability of a radiolabeled test agent due to SSAO catalyzed metabolism in a biological sample, the method comprising: (a) obtaining a biological sample comprising SSAO; (b) adding a radiolabeled test agent to the biological sample; (c) incubating the radiolabeled test agent with the biological sample for a predetermined period of time; and (d) measuring the amount of the radiolabeled test agent at the predetermined period of time wherein the percentage of radiolabeled test agent that has not been metabolized identifies the metabolic stability of the test agent in the presence of a biological sample comprising SSAO.

The skilled artisan can appreciate the usefulness of comparing the metabolic stability of a test agent in cells or cell lysates to the metabolic stability of the test agent in biological samples. Thus an embodiment of the present invention includes a method of determining the metabolic stability profile of a test agent, the method comprising (a) obtaining the value of metabolic stability of the test agent incubated in the presence of cells or cell lysate comprising expressed SSAO and (b) obtaining the value of metabolic stability of the test agent incubated in the presence of a biological sample comprising expressed SSAO wherein the value of metabolic stability of the test agent in the presence of the cells or cell lysate comprising expressed SSAO is compared to the value of metabolic stability of the test agent in the presence of the biological sample comprising SSAO providing the metabolic stability profile of the test agent.

Refinements such as using the present invention with high throughput screening (HIS) methods are well within the knowledge and capability of the skilled artisan and are considered embodiments of the invention. An embodiment of the invention is use in high throughput screening (HIS) methods. HTS is the automated, simultaneous testing of thousands of distinct chemical compounds in assays designed to model biological mechanisms or aspects of disease pathologies. More than one compound, e.g., a plurality of compounds, can be tested simultaneously. In one embodiment, the term HTS screening method refers to assays which test the metabolic stability of one compound in a plurality of biological samples or a plurality of compounds in one or more biological samples.

An embodiment of the present invention comprises an array of receptacles that can receive cells, cell lysates, bodily samples or other materials such as a methyleneamine or methyleneamine-like test agent under investigation. An array of receptacles can be any number of receptacles from at least one or more than one receptacle suitable for holding materials within the scope of the invention. Examples include but are not limited to flasks, culture dishes, slides, tubes such as 1.5 mL tubes, 12 well plates, 96 well plates, 384 well plates and miniaturized microtiter plates with perhaps 4000 receptacles (U.S. Patent Application 20050255580). The array of receptacles may be amendable to the addition of a protective covering thus preventing against entry of contaminants or evaporation of contents.

A further characteristic of the receptacles is that the receptacle may allow for analysis. Non-limiting examples include analysis by mass spectrometry or HPLC. However, there is not a limitation to receptacles that can be used within the scope of the present invention given that samples can be transferred to a suitable container for further analysis. A non-limiting example is to modify the method such that the method further comprises providing a second array of receptacles wherein one or more steps are performed in the second array of receptacles.

Liquid handling systems, analytical equipment such as fluorescence readers or scintillation counters and robotics for cell culture and sample manipulation are well known in the art. Mechanical systems such as robotic arms or "cherry-picking" devices are available to the skilled artisan. Commercial plate readers are available to analyze conventional 96-well or 384-well plates. Single sample, multiple sample or plate sample readers are available that analyze predetermined wells and generate raw data reports. The raw data can be transformed and presented in a variety of ways.

A further embodiment of the present invention is a kit comprising at least one element of an assay system to perform the methods disclosed herein and instructions for use. Thus, the components of the assay system may be provided separately or may be provided together in such a kit. Components of the assay system may be prepared and included in a kit according to methods that maximize the stability of the individual components. Such methods are familiar to those persons skilled in the art. For example, cells of the assay system may be provided as a suspension or the cells may be frozen or lyophilized. Additional components of the assay system may also be included such as buffers, containers for mixing the assay components such as microtiter plates or test tubes. The assay system can be provided in the form of a kit that includes instructions for performing the assay and instructions for data handling and interpretation.

The present invention is further described in the following examples, which do not limit the scope of the invention described in the claims. While the invention has been described and exemplified in sufficient detail for those skilled in this art to produce and use, various alternatives, modifications, and improvements should be apparent without departing from the spirit and scope of the invention. One skilled in the art readily appreciates that the present invention is well adapted to carry out the objective and obtain the ends and advantages mentioned, as well as those inherent therein. The examples that follow are descriptions of embodiments and are not intended as limitations on the scope of the invention. Modifications therein and other uses will occur to those skilled in the art. These modifications are encompassed within the spirit of the invention and are defined by the scope of the claims.

The present invention illustratively described herein may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be made by those skilled in the art, and that such modifications and variations are considered to be within the scope of this invention as defined by the appended claims.

EXAMPLE 1

A. Cloning and Expression of Human SSAO

1) In order to facilitate expression construct production, an initial pDONR221-full-length SSAO plasmid was generated as follows:

A first PCR was performed using gene-specific primers shown below. The forward primer has half of the att site (Invitrogen) and a Kozak sequence shown in bold. The reverse primer has the remaining half of the att site shown in bold. PCR was performed using human umbilical cord as the DNA template (prepared from RNA purchased from Biochain and Invitrogen's RT-PCR superscript II kit):

Initial Cloning Primers:

```
Forward (SEQ ID NO: 3):
5'-AAAAGCAGGCTTAGGAATGAACCAGAAGACAATCCTC-3'

Reverse (SEQ ID NO: 4):
5'-CAAGAAAGCTGGGTCCTAGTTGTGAGAGAAGCCCC-3'
```

A second PCR was then carried out using the universal primers shown below. The forward primer and the reverse primer included att site sequences (shown in bold) and vector sequences.

Universal Primer Sequences:

```
Forward (SEQ ID NO: 5):
5'-GGGGACAAGTTTGTACAAAAAAGCAGGCTTAGGA-3'

Reverse (SEQ ID NO: 6):
5'-GGGGACCACTTTGTACAAGAAAGCTGGGTC-3'
```

This second PCR product was cloned into pDONR221 using the Invitrogen BP reaction. Using this entry vector as template, six variations of human SSAO expression constructs were prepared; three forms (one full-length and two truncated) without tags and three with carboxyl-terminal 6×HIS tags to facilitate purification of the enzyme.

2) The Full-Length SSAO:

Sequences shown in bold on the forward primer and reverse primers indicate att site sequence.
Primer Sequences for Cloning Untagged, Full-Length SSAO:

```
Forward (SEQ ID NO: 7):
5'-AAAAGCAGGCTTAGGAATGAACCAGAAGACAATCCTC-3'

Reverse (SEQ ID NO: 8):
5'-CAAGAAAGCTGGGTCCTAGTTGTGAGAGAAGCCCCGTGG-3'
```

To add 3' 6×HIS before the stop codon the following primers were used:

Sequences shown in bold on the forward primer and the reverse primer indicate att site sequence, underlined sequences on the reverse primer indicate the 6×HIS tag.
Primer Sequences for Cloning Full-Length SSAO with C-Terminal 6×HIS Tag:

```
Forward (SEQ ID NO: 9):
5'-AAAAGCAGGCTTAGGAATGAACCAGAAGACAATCCTC-3'

Reverse (SEQ ID NO: 10):
5'-CAAGAAAGCTGGGTCCTAATGGTGATGGTGATGGTGGTTGTGAGA

GAAGCCCCGTGG-3'
```

3) T₁ (Gly27-Asn763) Representing the Enzyme Lacking the Membrane Anchoring Region:

Sequences shown in bold on the forward primer and the reverse primer indicate att site sequence, underlined sequences on the forward primer indicate additional N-terminal Met.
Primer Sequences for Cloning N-Terminal Truncated, Untagged SSAO:

```
Forward (SEQ ID NO: 11):
5'-AAAAGCAGGCTTAGGAATGGGCAGGGGTGGAGATGGGGGTG-3'

Reverse (SEQ ID NO: 12):
5'-CAAGAAAGCTGGGTCCTAGTTGTGAGAGAAGCCCC-3'
```

To add 3' 6×HIS before the stop codon the following primers were used:

Sequences shown in bold on the forward primer and the reverse primer indicate att site sequence, underlined sequences on the forward primer indicate additional N-terminal Met, and underlined sequences on the reverse primer indicate the 6×HIS tag.
Primer Sequences for Cloning N-Terminal Truncated, C-Terminal 6×HIS Tag SSAO:

```
Forward (SEQ ID NO: 13):
5'-AAAAGCAGGCTTAGGAATGGGCAGGGGTGGAGATGGGGGTG-3'

Reverse (SEQ ID NO: 14):
5'-CAAGAAAGCTGGGTCCTAATGGTGATGGTGATGGTGGTTGTGAGA

GAAGCCCCGTGG-3'
```

4) T₂ (Met211-Asn763) Representing the Putative Catalytic Domain.

Sequences shown in bold on the forward primer and the reverse primer indicate att site sequence, and underlined sequences on the forward primer indicate additional N-terminal Met.
Primer Sequences for Cloning Catalytic Domain of Untagged SSAO:

```
Forward (SEQ ID NO: 15):
5'-AAAAGCAGGCTTAGGAATGACCACGGCTCCCCGTGGTC-3'

Reverse (SEQ ID NO: 16):
5'-CAAGAAAGCTGGGTCCTAGTTGTGAGAGAAGCCCC-3'
```

To add 3' 6×HIS before stop codon the following primers were used:

Sequences shown in bold on the forward primer and the reverse primer indicate att site sequence, underlined sequences on the forward primer indicate additional N-terminal Met, underlined sequences on the reverse primer indicate the 6×HIS tag.
Primer Sequences for Cloning Catalytic Domain of SSAO with C-Terminal 6×HIS Tag:

```
Forward (SEQ ID NO: 17):
5'-AAAAGCAGGCTTAGGAATGACCACGGCTCCCCGTGGTC-3'

Reverse (SEQ ID NO: 18):
5'-CAAGAAAGCTGGGTCCTAATGGTGATGGTGATGGTGGTTGTGAGA

GAAGCCCCGTGG-3'
```

The expression constructs were prepared by cloning these PCR products into the pCDNA5-FRT-To-DEST vector (Invitrogen, Gateway System™). The forward and reverse DNA sequence of each construct was confirmed including expressed sequences and at least 100 base pairs either side of this. Stable cell lines for Flp-In CHO, Flp-In CHO T-Rex, and Flp-In HEK 293 (Invitrogen, Flp-In system™) were generated using these 6 constructs according to manufacturer's instructions. Cells were co-transfected with the regulatory vector, pOG44, and each of the pCDNA5-FRT-To-DEST constructs using Lipfectamine (Invitrogen) according to manufacturer's instructions. Thus, 18 cell lines were generated: CHO Flp-In full-length SSAO; CHO Flp-In full-length SSAO with C-terminal 6×HIS tag; CHO Flp-In T₁ SSAO; CHO Flp-In T₁ SSAO with C-terminal 6×HIS tag; CHO Flp-In T₂ SSAO; CHO Flp-In T₂ SSAO with C-terminal 6×HIS tag; CHO T-Rex Flp-In full-length SSAO; CHO T-Rex Flp-In full-length SSAO with C-terminal 6×HIS tag; CHO T-Rex Flp-In T₁ SSAO; CHO T-Rex Flp-In T₁ SSAO with C-terminal 6×HIS tag; CHO T-Rex Flp-In T₂ SSAO; CHO Flp-In T₂ SSAO with C-terminal 6×HIS tag; HEK 293 Flp-In full-length SSAO; HEK 293 Flp-In full-length SSAO with C-terminal 6×HIS tag; HEK 293 Flp-In T₁ SSAO; HEK 293 Flp-In T₁ SSAO with C-terminal 6×HIS tag; HEK 293 Flp-In T₂ SSAO; HEK 293 Flp-In T₂ SSAO with C-terminal 6×HIS tag.

Adherent CHO cells were cultured at 37° C., 5% $CO_2$ in media containing Ham's F12, 10% fetal bovine serum, 2 mM L-glutamine, 1% Penicillin/Streptomycin, 300 μM hygromycin B. Adherent HEK 293 cells were cultured at 37° C., 5% $CO_2$ in D-MEM (high glucose), 10% fetal bovine serum, 2 mM L-glutamine, and 200 μM hygromycin B. Stable transformants were identified by loss of zeocin resistance. Once the cells were 80% confluent, SSAO expression was induced by the addition of Tetracycline to 1 μg/mL. Following 18 hours, the cells were harvested using a trypsin treatment of 3 minutes, at room temperature. Cells were washed 3 times in phosphate buffered saline before flash freezing in liquid nitrogen.

For the preparation of cell lysate for activity testing, frozen cell pellets were resuspended in lysate buffer containing 10 mM Tris-HCl (pH 7.2), 150 mM NaCl, 1.5 mM $MgCl_2$, 1% v/v NP-40 and incubated for 15 minutes on ice. Lysate was cleared by centrifugation 800×g for 10 minutes, 4° C. and stored in aliquots at −80° C. until use. Proteins were determined using Pierce Coomassie Protein Reagent, according to manufacturer's instructions.

B. Testing the Recombinant Protein for Enzymatic Activity (i). Sample Preparation.

For each assay run, 1 mL of cell lysate (1.5 mg/mL protein) was mixed with benzylamine to 2000 ng/mL final concentration. At each corresponding time point, 20 of the incubation mixture was transferred to a microcentrifuge tube (1.7 mL) and mixed with 50 µL of acetonitrile. The tubes were vortex mixed briefly to ensure complete mixing and then centrifuged at 10,000×g for 5 minutes. The supernatant was removed and 50 µL was transferred to an autosampler vial and mixed with 50 µL of water before LC/MS/MS analysis. Benzylamine remaining in the lysate was analyzed with LC/MS/MS method.

(ii). Analysis

LC/MS/MS analysis was performed with a PE Sciex API 3000 mass spectrometer under the following conditions listed below and in Tables 1 and 2:

Analytical column: Jupiter C-4, 5 µM, 50×2.1 mm

Column temperature: ambient

Flow rate: 0.2 mL/min

Injection volume: 15 µL

TABLE 1

| Mobile Phase Gradient | | |
| --- | --- | --- |
| Time (min) | SolutionA (%) | SolutionB (%) |
| 0 | 40 | 60 |
| 0.1 | 95 | 5 |
| 2.9 | 95 | 5 |
| 3.0 | 40 | 60 |
| 6.0 | 40 | 60 |

SolutionA was 90% methanol in water, SolutionB was 10 mM ammonium acetate buffer, pH 7.0

Divert valve: 0-1.5 min to waste, 1.5-5 min to MS detector

TABLE 2

| LC/MS/MS | | | |
| --- | --- | --- | --- |
| Compound | RT (min) | Mass transition | |
| Benzylamine | 2.74 | 108.1 to 65.1 | +Ve |

(iii) Results of cell lysate LC/MS/MS analysis are shown in Table 3.

TABLE 3

| SSAO Enzymatic Activity in Cell Lines Expressing Full-length or Truncated SSAO | | | | | |
| --- | --- | --- | --- | --- | --- |
| Source of Cell Lysate | SSAO Expressed | Tag | Benzylamine Remaining (%) | | |
| | | | 0 min | 10 min | 2 h |
| Control CHO | none | None | 100 | 111 | 110 |
| Control CHO Flp-In | none | None | 100 | 104 | 99 |
| CHO Flp-In | Full-length | None | 100 | 1 | 1 |
| CHO Flp-In | Full-length | C-terminal 6xHIS | 100 | 101 | 73 |
| CHO Flp-In | T1 | None | 100 | 109 | 103 |
| CHO Flp-In | T1 | C-terminal 6xHIS | 100 | 101 | 98 |
| CHO Flp-In | T2 | None | 100 | 105 | 98 |
| CHO Flp-In | T2 | C-terminal 6xHIS | 100 | 108 | 102 |
| CHO Flp-In T-Rex | None | None | 100 | 104 | 99 |
| CHO Flp-In T-Rex | Full-length | None | 100 | 6 | 0 |
| CHO Flp-In T-Rex | Full-length | C-terminal 6xHIS | 100 | 94 | 59 |
| CHO Flp-In T-Rex | T1 | One | 100 | 104 | 92 |
| CHO Flp-In T-Rex | T1 | C-terminal 6xHIS | 100 | 95 | 93 |
| CHO Flp-In T-Rex | T2 | None | 100 | 97 | 83 |
| CHO Flp-In T-Rex | T2 | C-terminal 6xHIS | 100 | 100 | 97 |
| HEK293 control | none | None | 100 | 106 | 123 |
| HEK293 | Full-length | None | 100 | 58 | 2 |
| HEK293 | Full-length | C-terminal 6xHIS | 100 | 105 | 98 |
| HEK293 | T1 | None | 100 | 105 | 102 |
| HEK293 | T1 | C-terminal 6xHIS | 100 | 111 | 103 |
| HEK293 | T2 | None | 100 | 113 | 101 |
| HEK293 | T2 | C-terminal 6xHIS | 100 | 100 | 117 |

The active lysates from CHO Flp-In, CHO Flp-In T-Rex or HEK293 Flp-In expressing full-length SSAO (untagged) were subsequently tested and activity confirmed (Table 4). Since the most active SSAO cell lines was the CHO Flp-In expressing the full-length (untagged) SSAO, this preparation was used for subsequent activity testing.

TABLE 4

| SSAO Enzymatic Activity in Cell Lines Expressing Full-length SSAO | | | |
| --- | --- | --- | --- |
| Cell Type Expressing Full-length SSAO (untagged) | Benzylamine Remaining (%) | | |
| | 0 min | 10 min | 30 min |
| HEK293 Flp-In | 100 | 50 | 9 |
| CHO Flp-In | 100 | 9 | 1 |
| CHO Flp-In T-Rex | 100 | 16 | 1 |

EXAMPLE 2

Optimising LCMS/MS Assay Conditions

The Amplex Red assay (a commercially available assay), was used initially to measure the specific activity of the recombinant human SSAO. Amplex Red is a colorless and nonfluorescent derivative of dihydroresorufin. In the presence of amine oxidases and SSAO, the Amplex Red reacts with $H_2O_2$ to produce the highly fluorescent product, resorufin. Resorufin has an excitation maximum at 563 nm and emission maximum at 587 nm and the assay can be quantified by reading the microtitre plate at 587 nm. The specific activity of recombinant SSAO was determined to be 280 pmol/min/mg protein and this was determined to be equivalent to the specific activity of SSAO found in human lung tissue. For subsequent assays to profile compounds in the LC/MS/MS assay, recombinant human SSAO (rhSSAO) was used at this defined specific activity.

The LC/MS/MS assay as described above was used to evaluate the susceptibility of compound A to metabolism by rhSSAO. The chemical structure of compound A is shown in FIG. 3 (U.S. Pat. No. 6,977,263 B2 generically encompasses molecules and methods of making the same). Compound A shown in Table 5 was incubated at 37° C. with rhSSAO (having a defined specific activity that is compatible with that found in human tissues as described above) for 4 hours initially or for 24 hours. At time zero and time 4 hours (or 24 hours), an aliquot of the sample was removed and quenched with acetonitrile. The samples were then analyzed by LC/MS/MS to measure the amount of parent compound remaining at 24 hours compared to that present at time zero.

The values shown in Table 5 are percent of parent compound remaining at the various times indicated following incubation with rhSSAO.

TABLE 5

Percent of Parent Compound Remaining
Following Incubation with rhSSAO
% Parent Compound Remaining

| Compound | 0 h (%) | 4 h (%) | 24 h (%) |
|---|---|---|---|
| A | 100 | 25 | 3.2 |

EXAMPLE 3

Testing of Metabolic Stability of Compound A in Supernatant Preparations of Human and Animal Tissue Homogenates (i) Tissues Used The following tissues were used: lung, liver, and ileum from guinea pig, cynomolgus monkey, and human; artery from guinea pig and monkey; and umbilical cord from human.

(ii) Tissue Preparation

Tissues were processed to obtain supernatants. Briefly, the excised tissues were rinsed immediately with copious amounts of physiological saline (prechilled to 4° C.) to remove blood. Pooled tissues were homogenized in chilled 0.01 M sodium phosphate buffer at pH 7.4 (10 mL per g tissue) with a Polytron. The homogenate was treated with Triton X-100 at an added concentration of ca. 1% under continuous gentle shaking for 2 hours at 4° C. and then centrifuged (4° C., 15 minutes, 3000×g). The supernatant was carefully separated and aliquoted into 2 mL portions and frozen at approximately −80° C. until use.

(iii) Optimization of Incubation Conditions with Test Compound

All incubations were conducted at 37° C. using a prewarmed water bath. $^{14}$C-radiolabeled test compound were incubated at 1 or 10 μM. Preliminary incubations were performed for each tissue/compound combination to select the appropriate incubation durations. Incubation durations of 1.5 to 6 hours were then used. Sufficient incubation volume was used to allow for at least five serial samples during the incubation duration. Individual aliquots (1 mL) taken from the incubation mixture were immediately quenched with two volumes of acetonitrile and the quenched mixtures were freeze-dried. The freeze-dried samples were either reconstituted immediately for sample analysis or stored at approximately −80° C. until analysis. Reconstitution was performed with a 500 μL mixture (90% 20 mM ammonium acetate, pH 4.0 and 10% methanol (v/v)). After centrifugation, 100 μL reconstituted sample was injected for high performance liquid chromatographic (HPLC) separation followed by radiomatic detection.

(iv) Data Analysis and Calculations

Reconstituted samples from incubations were analyzed by HPLC followed by radiomatic detection. The identity of the test compound and respective benzylaldehyde and acid metabolites were verified by matching the retention times with the reference standards of the parent compound and their respective metabolites. The amount of the test compound remaining is calculated as the percent of the radioactivity of the parent peak in the total radioactivity of the radiochromatogram of a reconstituted sample. The percent of test compound remaining versus incubation time showed first-order kinetics when plotted on a log-linear scale. The first-order rate constant was calculated for individual incubations as the slope between the logarithm of the test compound remaining versus time based on least square linear regression analysis.

(v) Results of Test Compound Metabolic Stability in Tissue Preparations

The first-order rate constant (1/h) for the metabolic degradation of the test compound is listed in Table 6. Assuming that the metabolism followed Michaelis-Menten kinetics, the approximation to first-order kinetics for up to 10 μM implied that $K_m$>>μM for the enzymatic reaction.

TABLE 6

Metabolic Stability of Compound A in Tissue Preparations

| | | Compound A | |
|---|---|---|---|
| Species | Tissue | 1 μM | 10 μM |
| Human | Liver | 0.418 | 0.365 |
| | Ileum | 0.352 | 0.353 |
| | Lung | 0.675 | 0.706 |
| | Umbilical cord | 0.688 | 0.697 |
| Guinea pig | Liver | 0.318 | 0.305 |
| | Ileum | 0.0775 | 0.0782 |
| | Lung | 0.747 | 0.709 |
| | Artery | 0.127 | 0.111 |
| Monkey | Liver | 2.05 | 2.64 |
| | Ileum | 0.328 | 0.277 |
| | Lung | 0.177 | 0.208 |
| | Artery | 0.835 | 0.673 |

As shown Table 6, the present invention demonstrates a good correlation between the tissue data and the observed clinical metabolic profile of compound A. Compared to using only human plasma stability measurements, the present invention can better reflect human SSAO stability of a pharmaceutical agent under physiological conditions and is a more relevant predictive tool for guiding the is selection of and the pharmaceutical development of clinical candidates.

What is claimed is:

1. A method of determining the relative metabolic stability profile of a test agent due to semicarbazide-sensitive amine oxidase (SSAO) catalyzed metabolism in recombinant cultured cells expressing full-length SSAO and in a biological sample comprising SSAO, wherein the test agent is a drug candidate and the metabolic stability of the test agent due to SSAO catalyzed metabolism is unknown, the method comprising:

a) determining the metabolic stability of the test agent in the presence of recombinant cultured cells expressing full-length SSAO; by:
  i) adding the test agent to the recombinant cultured cells;
  ii) incubating the test agent with the recombinant cultured cells for a predetermined period of time;
  iii) measuring the amount of the test agent remaining in the presence of the recombinant cultured cells at the predetermined period of time; and
  iv) comparing the amount of the test agent remaining in the presence of the recombinant cultured cells at the predetermined period of time to a control to determine the metabolic stability of the test agent in the presence of recombinant cultured cells expressing full-length SSAO;

b) determining the metabolic stability of the test agent in the presence of a biological sample comprising SSAO by:
  i) adding the test agent to the biological sample;
  ii) incubating the test agent with the biological sample for a predetermined period of time;
  iii) measuring the amount of the test agent remaining in the presence of the biological sample at the predetermined period of time; and
  iv) comparing the amount of the test agent remaining in the presence of the biological sample at the predetermined period of time to a control to determine the metabolic stability of the test agent in the presence of a biological sample comprising SSAO; and c) comparing the metabolic stability of the test agent in the presence of recombinant cultured cells expressing full-length SSAO to the metabolic stability of the test agent in the presence of a biological sample comprising SSAO to determine the relative metabolic stability profile of the test agent.

2. A method of determining the relative metabolic stability profile of a radiolabeled test agent due to semicarbazide-sensitive amine oxidase (SSAO) catalyzed metabolism in recombinant cultured cells expressing full-length SSAO and in a biological sample comprising SSAO, wherein the test agent is a drug candidate and the metabolic stability of the test agent due to SSAO catalyzed metabolism is unknown, the method comprising:
- a) determining the metabolic stability of the radiolabeled test agent in the presence of recombinant cultured cells expressing full-length SSAO by:
  - i) adding the radiolabeled test agent to the recombinant cultured cells;
  - ii) incubating the radiolabeled test agent with the recombinant cultured cells for a predetermined period of time;
  - iii) measuring the amount of the radiolabeled test agent remaining in the presence of the recombinant cultured cells at the predetermined period of time; and
  - iv) comparing the amount of the radiolabeled test agent remaining in the presence of the recombinant cultured cells at the predetermined period of time to a control to determine the metabolic stability of the radiolabeled test agent in the presence of recombinant cultured cells expressing full-length SSAO;
- b) determining the metabolic stability of the radiolabeled test agent in the presence of a biological sample comprising SSAO by:
  - i) adding the radiolabeled test agent to the biological sample;
  - ii) incubating the radiolabeled test agent with the biological sample for a predetermined period of time;
  - iii) measuring the amount of the radiolabeled test agent remaining in the presence of the biological sample at the predetermined period of time; and
  - iv) comparing the amount of the radiolabeled test agent remaining in the presence of the biological sample at the predetermined period of time to a control to determine the metabolic stability of the radiolabeled test agent in the presence of a biological sample comprising SSAO; and
- c) comparing the metabolic stability of the radiolabeled test agent in the presence of recombinant cultured cells expressing full-length SSAO to the metabolic stability of the radiolabeled test agent in the presence of a biological sample comprising SSAO to determine the relative metabolic stability profile of the radiolabeled test agent.

3. The method of either claim 1 or 2, wherein the cultured cells expressing SSAO are produced by transient or stable transfection of the cells with DNA encoding SSAO.

4. The method of claim 3, wherein the DNA comprises the nucleotide sequence of SEQ ID NO: 2.

5. The method of claim 3, wherein the DNA encodes the amino acid sequence of SEQ ID NO: 1.

6. The method of either claim 1 or 2, wherein the cultured cells expressing SSAO are prokaryotic cells.

7. The method of either claim 1 or 2, wherein the cultured cells expressing SSAO are eukaryotic cells.

8. The method of either claim 1 or 2, wherein the biological sample is a blood, plasma, serum, artery, umbilical cord, liver, ileum, or lung sample.

9. The method of claim 8, wherein the biological sample is from a human subject.

10. The method of claim 9, wherein the human subject is manipulated prior to obtaining the biological sample from the human subject.

11. The method of claim 10, wherein the manipulation of the human subject is treatment with one or more drugs, induction of one or more aspects of a disease state, surgical manipulation, or genetic alteration.

12. The method of claim 8, wherein the biological sample is from a non-human subject.

13. The method of either claim 1 or 2, wherein the amount of test agent is determined by mass spectrometry, high-pressure liquid chromatography, liquid chromatography/mass spectrometry, liquid chromatography/mass spectrometry/mass spectrometry, or liquid chromatography/radiomatic detection.

14. The method of either claim 1 or 2, wherein at least one step is performed by a robotic device.

15. The method of either claim 1 or 2, wherein the metabolic stability of the test agent is determined by measuring one or more metabolites of the test agent in addition to or in place of measuring the test agent.

16. The method of either claim 1 or 2, wherein the control is a condition in which the test agent is incubated for the predetermined period of time in the absence of cells expressing SSAO or in cell lysates obtained from such cells.

17. The method of either claim 1 or 2, wherein the control is a compound metabolized by SSAO that is incubated with the cells expressing SSAO for the predetermined period of time.

18. The method of claim 17, wherein the compound is benzylamine.

19. The method of either claim 1 or 2, wherein the control is a compound resistant to metabolism by SSAO that is incubated with the cells expressing SSAO for the predetermined period of time.

20. The method of claim 19, wherein the compound is benzoic acid.

21. The method of either claim 1 or 2, wherein the control is a condition in which the test agent is incubated for the predetermined period of time in the absence of cells expressing SSAO and hydralazine.

* * * * *

UNITED STATES PATENT AND TRADEMARK OFFICE
CERTIFICATE OF CORRECTION

PATENT NO.        : 8,883,410 B2
APPLICATION NO.   : 13/680068
DATED             : November 11, 2014
INVENTOR(S)       : Adedayo Adedoyin et al.

Page 1 of 1

It is certified that error appears in the above-identified patent and that said Letters Patent is hereby corrected as shown below:

On the title page, item (75), in column 1, in "Inventors", line 1, delete "Caims" and insert -- Cairns --, therefor.

On the title page, item (56), in column 2, References Cited under "Other Publications", line 6, delete "Boold," and insert -- Blood, --, therefor.

On the title page, item (56), in column 2, References Cited under "Other Publications", line 7, delete "transpermus" and insert -- tresperimus --, therefor.

On the title page, item (56), in column 2, References Cited under "Other Publications", line 13, delete "PCT/US2008/05045" and insert -- PCT/US2008/050456, --, therefor.

On the title page, item (56), in column 2, References Cited under "Other Publications", line 37, delete "activity" and insert -- activity of --, therefor.

On the title page 2, item (56), in column 2, References Cited under "Other Publications", line 19, delete "faminas,"" and insert -- laminas," --, therefor.

In the Specification

In column 9, line 12, delete "(HIS)" and insert -- (HTS) --, therefor.

In column 9, line 15, delete "(HIS)" and insert -- (HTS) --, therefor.

In column 13, line 24, delete "20" and insert -- 20 μL --, therefor.

In column 16, line 66, delete "this is selection" and insert -- this selection --, therefor.

Signed and Sealed this
Twenty-first Day of April, 2015

Michelle K. Lee
*Director of the United States Patent and Trademark Office*